United States Patent
Schulze-Ganzlin et al.

(10) Patent No.: US 11,903,753 B2
(45) Date of Patent: Feb. 20, 2024

(54) DENTAL X-RAY IMAGING SYSTEM FOR PRODUCING INTRAORAL X-RAY IMAGES

(71) Applicants: DENTSPLY SIRONA INC., York, PA (US); SIRONA DENTAL SYSTEMS GMBH, Bensheim (DE)

(72) Inventors: Ulrich Schulze-Ganzlin, Lorsch (DE); Kai Lindenberg, Wersau (DE)

(73) Assignee: DENTSPLY SIRONA INC., York, PA (US)

(*) Notice: Subject to any disclaimer, the term of this patent is extended or adjusted under 35 U.S.C. 154(b) by 342 days.

(21) Appl. No.: 17/417,856

(22) PCT Filed: Dec. 16, 2019

(86) PCT No.: PCT/EP2019/085389
§ 371 (c)(1),
(2) Date: Jun. 24, 2021

(87) PCT Pub. No.: WO2020/136033
PCT Pub. Date: Jul. 2, 2020

(65) Prior Publication Data
US 2022/0061787 A1    Mar. 3, 2022

(30) Foreign Application Priority Data
Dec. 28, 2018 (EP) .................................. 18248277

(51) Int. Cl.
*A61B 6/14* (2006.01)
*A61B 6/00* (2006.01)

(52) U.S. Cl.
CPC ............ *A61B 6/145* (2013.01); *A61B 6/5235* (2013.01); *A61B 6/5264* (2013.01); *A61B 6/542* (2013.01); *A61B 6/583* (2013.01)

(58) Field of Classification Search
CPC ...... A61B 6/145; A61B 6/5235; A61B 6/5264; A61B 6/542; A61B 6/583
See application file for complete search history.

(56) References Cited

U.S. PATENT DOCUMENTS

| 2006/0193436 A1 | 8/2006 | Schick |
| 2007/0025503 A1 | 2/2007 | Hemmendorff |

(Continued)

FOREIGN PATENT DOCUMENTS

| EP | 3673810 B1 | 9/2023 |
| JP | H09056707 A | 3/1997 |

(Continued)

OTHER PUBLICATIONS

International Search Report; PCT/EP2019/085389; Feb. 7, 2020 (completed); dated Jun. 23, 2020.

(Continued)

*Primary Examiner* — Courtney D Thomas
(74) *Attorney, Agent, or Firm* — DENTSPLY SIRONA INC.

(57) ABSTRACT

The invention relates to a dental x-ray imaging system for producing intraoral x-ray images, in particular of dental patient tissue, with the aid of an intraoral x-ray sensor, which can be placed in the oral cavity in the beam path of an x-ray emitter positioned outside the oral cavity, wherein the x-ray imaging system is configured to record two or more temporally sequential individual x-ray images and to create an overall x-ray image from said individual images in such a way that the results of the exposures of the x-ray images are combined and a motion occurring between and/or during the sequential individual x-ray images is compensated.

15 Claims, 3 Drawing Sheets

(56) References Cited

U.S. PATENT DOCUMENTS

| | | |
|---|---|---|
| 2011/0235874 A1 | 9/2011 | Siren |
| 2012/0307965 A1 | 12/2012 | Bothorel |
| 2016/0209336 A1 | 7/2016 | Sung |
| 2017/0281110 A1* | 10/2017 | Mandelkern ......... A61B 6/5217 |

FOREIGN PATENT DOCUMENTS

| | | |
|---|---|---|
| JP | 2000501973 A | 2/2000 |
| JP | 2002306471 A | 10/2002 |
| JP | 2009515573 A | 4/2009 |
| JP | 2011056170 A | 3/2011 |
| JP | 2012533339 A | 12/2012 |
| JP | 2016193177 A | 11/2016 |
| WO | 2013031667 A1 | 3/2013 |

OTHER PUBLICATIONS

Written Opinion of the International Searching Authority; PCT/EP2019/085389; Feb. 7, 2020 (completed); dated Jun. 23, 2020.
International Preliminary Report on Patentability; PCT/EP2019/085389; Feb. 7, 2020 (completed); dated Jun. 23, 2020.

* cited by examiner

DENTAL X-RAY IMAGING SYSTEM FOR PRODUCING INTRAORAL X-RAY IMAGES

CROSS-REFERENCE TO RELATED APPLICATIONS

This is a National Phase application of International Application No. PCT/EP2019/085389 filed Dec. 16, 2019, which claims the benefit of and priority to European Patent Application Number EP18248277.8 filed on Dec. 28, 2018 which are herein incorporated by reference for all purposes.

TECHNICAL FIELD

The invention relates to a dental x-ray imaging system for producing intraoral x-ray images, in particular of dental patient tissue, with the aid of an intraoral x-ray sensor, which can be placed in the oral cavity of a patient in the beam path of an, in particular handheld, x-ray emitter positioned outside the oral cavity.

BACKGROUND OF THE INVENTION

A variety of x-ray-based imaging systems are available in the field of dental radiology, whereby said imaging systems can be subdivided into extraoral and intraoral x-ray systems. Extraoral x-ray technology (EO x-raying) is typically used for two-dimensional panoramic imaging, for remote x-ray imaging, or for three-dimensional digital volume tomography (DVT). Intraoral x-ray systems (IO x-raying), on the other hand, are generally used for imaging a limited area of the jaw, for example one or more teeth.

When using intraoral x-ray technology, the x-ray sensor, i.e. the x-ray detector or, in the case of an analog recording, the x-ray film, is placed inside the oral cavity of the patient, so that x-ray radiation can penetrate the relevant region of the jaw from outside the oral cavity and expose the x-ray sensor in the mouth. An x-ray tube serves as part of an x-ray emitter, which can be attached to a movable support arm, for example, or can also be designed as a mobile handheld device, to produce the x-ray radiation.

On the one hand, care must be taken to ensure the proper positioning of the x-ray sensor and the x-ray emitter in relation to one another and to the jaw region to be irradiated in order to create high-quality intraoral x-ray images and thus make the best dental diagnosis possible. On the other hand, proper and coordinated setting and control of the radiation and detection parameters is important.

Depending on the size of the patient, the jaw region, and the emitter output, the exposure time when using modern detectors for intraoral diagnostic radiology can, for example, be between 40 and 200 milliseconds. The longer this exposure time is, the greater are the influences of motions of emitter, sensor, and patient, which adversely affect the resolution of the resulting x-ray image and can lead to motion blur or motion artifacts. Such lack of sharpness or artifacts caused by motion of the patient, the sensor and/or the emitter during the exposure can show up in the image as visible blurring.

When using x-ray emitters with a fixedly mounted support arm, the motion of the emitter at least can be minimized, but motions of the sensor and the patient, which can lead to motion blur, remain. On the other hand, when using handheld emitters (handheld x-ray emitters), the motion of the emitter can also lead or contribute to motion blur because intraoral radiography is an expositing technique. The common use of relatively low dose outputs is an additional complicating factor when using handheld emitters. Exposure times are therefore generally longer, which further promotes undesirable motion blur and/or artifacts.

Another problem that can occur in intraoral imaging is locally insufficient or, in the worst case, completely absent exposure of the x-ray sensor. Such exposition can in particular occur in the event of an incorrect alignment of the emitter, the sensor, and the patient tissue relative to one another. This can possibly again also be attributed to undesirable motions occurring during or even before exposure. This problem is exacerbated when handheld x-ray emitters are used. The x-rays, which are typically limited to a specific diameter by collimation, consequently reach the sensor surface only partly or perhaps not at all. Despite using the full patient dose, this can result in no usable image being produced.

SUMMARY OF THE INVENTION

In summary, it can be stated that the recording of x-ray images for intraoral diagnostics, in particular when using handheld emitters, still has room for improvement.

The underlying object of the invention is therefore to facilitate the creation of intraoral x-ray images, so that motion blur or motion artifacts are minimized or avoided and x-ray recordings having the highest possible precision and sharpness and showing the greatest possible number of anatomical details can be obtained.

A further aspect of said object is to minimize or avoid x-ray exposition or, if there is exposition, at least to keep the patient dose low. It is therefore also an aspect of said object to increase the likelihood of obtaining a usable x-ray image.

The object of the invention is achieved with the subject matter of the independent claims. Advantageous further developments of the invention are defined in the dependent claims.

The invention provides a dental x-ray imaging system for producing an intraoral x-ray image with reduced motion blur.

The x-ray imaging system comprises an intraoral x-ray sensor, which can be placed behind patient tissue to be irradiated inside the mouth of a patient in the beam path of an x-ray emitter positioned outside the mouth of the patient.

The intraoral x-ray sensor is in particular embodied as a sensor (detector) having a matrix structure, which is configured to break an x-ray image projection up into pixels. The detected signal strength per pixel preferably corresponds to the locally absorbed x-ray beam energy. The x-ray imaging system can further comprise an x-ray emitter, for example embodied as a handheld device, as will be explained in more detail below.

According to the invention, the x-ray imaging system is configured to record at least two and preferably several or even a large number of temporally sequential individual x-ray images of the patient tissue during respective exposures, wherein these individual x-ray images are in particular recorded during one recording session.

The temporally sequential individual x-ray images are generally the result of individual exposures, whereby, as it will be discussed later, continuous radiation generated by the emitter may also be an option. It is worth mentioning that the temporally sequential individual x-ray images are in particular insufficiently exposed, i.e. fall short of a predefined exposure range or level, for example, and are therefore generally not yet used for medical diagnosis.

The temporally sequential individual x-ray images may also not yet be further processed, so that they are still present in the form of raw data, for example, which can advantageously still be corrected with the aid of histogram compensation and/or with respect to sensor inadequacies.

According to the invention, the x-ray imaging system is configured to create an overall x-ray image from the or some of the temporally sequential individual x-ray images such that (i) on the one hand, the respective exposures, or, more specifically, the results of the respective exposures are merged and (ii) on the other hand, motion occurring between and/or during the sequential individual x-ray images is compensated. It is thus possible to obtain an exposure-blended intraoral x-ray image with reduced motion blur.

The obtained intraoral x-ray image combines the image information of the two or more temporally sequential individual x-ray images and is in particular sufficiently exposed, i.e. achieves a predefined exposure range, for example, and can therefore generally be used for diagnosis. In other words, the x-ray imaging system is in particular configured to merge the two or more temporally sequential individual x-ray images, which can originate from pre- and main exposures, for example, to one final intraoral x-ray image in a later step. This "summed" final IO x-ray image preferably has a predefined exposure range (intensity), which represents a compromise between radiation hygiene and sensor saturation on the one hand and the expected image quality for a reliable diagnosis on the other hand.

The use of the invention thus advantageously avoids the long overall exposure that would certainly ensure an exposure range suitable for the diagnosis, but is sensitive to shaking and motion blur. Motion blur, which would otherwise occur during long overall exposure due to motion of focus, patient, and/or detector and is expressed in "smearing" at least in parts of the x-ray image, can thus successfully be minimized or avoided. The advantage of reduced motion blur comes into play particularly for handheld x-ray emitters, but it is generally applicable as a basic principle.

Motion compensation is carried out in the course of or prior to merging the temporally sequential individual x-ray images. Motion, for example of focus, patient, and/or detector, which occurs between and/or during the individual x-ray images, is thus compensated. In this way, effects of the motion, which would otherwise lead to motion blur or motion artifacts, can advantageously be reduced or avoided. This also means that the likelihood of an IO x-ray image usable for diagnosis, in particular in the case of handheld emitters, is increased. Consequently, there is no need for further x-ray images, which in turn also reduces the radiation exposure for patients.

Motion compensation can in particular be achieved by using a motion compensator. As will be explained in more detail further below, a hardware solution can in principle be provided to bring about an oppositely-directed motion, or motion compensation preferably takes place in a later step, i.e. after recording the individual x-ray images. In this case, a compensation of the motion in particular refers to the compensation of the effect of a motion on the individual x-ray images.

As already mentioned, the temporally sequential individual x-ray images can be available unprocessed, as raw sensor data. However, the x-ray imaging system preferably comprises an image optimizer that is configured to optimize and correct the individual images.

The image optimizer can in particular be configured to correct the individual images with respect to sensor inadequacies. To do this, the x-ray imaging system can be configured to record a dark current image in which the sensor is not exposed with x-ray radiation, for example prior to the first individual image and/or after the last individual image. The image optimizer can then use one or more dark current images to optimize the or at least one of the sequential x-ray images possibly still present in the form of raw data and/or the overall x-ray image of the patient tissue.

To do this, the image optimizer can in particular be configured to perform a calculation based on x-ray sensor signal values associated with pixels of a dark current image on the one hand, and x-ray sensor signal values associated with pixels of one of the sequential x-ray images and/or of the overall x-ray image of the patient tissue on the other hand. In other words, the image optimizer can be configured to offset x-ray sensor signal values associated with pixels of a dark current image with x-ray sensor signal values associated with pixels of the sequential x-ray image and/or of the overall x-ray.

The image optimizer can additionally be configured to perform further corrections, for example a histogram compensation and/or a linearization of the brightness values associated with the pixels.

An image optimizer included in the x-ray imaging system can be embodied as a hardware component, which preferably contains an FPGA module or functionally identical or similar module or is embodied as such. On the other hand, it can also be provided that the image optimizer or parts thereof are embodied as a computer program, wherein the program includes instructions that, when executed by a computer, cause said computer to optimize at least one of the temporally sequential individual x-ray images and/or the overall x-ray image of the patient tissue, in particular by means of a dark current image.

The x-ray imaging system can further comprise an image selector, wherein the image selector is configured to select or reject specific x-ray images from the or some of the sequential individual x-ray images.

The image selector can in particular be configured to evaluate the or some of the sequential individual x-ray images using predefined criteria in order to select from among them suitable, in particular sufficiently congruent, x-ray images or reject unsuitable, in particular overly incongruent x-ray images.

By selecting and/or rejecting x-ray images, a motion compensation can be achieved. Individual images can, in a sense, be "shaken in" until a certain quality measure is achieved. An image selector configured in this way is particularly suitable when several or a large number of temporally sequential individual x-ray images are recorded.

A minimum degree of congruence or incongruence can be used as a criterion for selecting and/or rejecting individual x-ray images. The brightness values, for example, that are associated with the, or for example several, uniformly or statistically distributed pixels, can be used for this purpose.

The image selector can be embodied as a hardware component, preferably comprising or embodied as an FPGA module or functionally identical or similar module. It can also be provided that the image selector or parts thereof are embodied as a computer program, wherein the program includes instructions that, when executed by a computer, cause said computer to select and/or reject individual x-ray images.

The x-ray imaging system further preferably comprises a motion detector, wherein said motion detector is configured to detect motion occurring between and/or during the or some of the sequential individual x-ray images.

Within the context of this application, detection can generally be the mere determination of the existence of a motion. A motion detector that detects the existence or absence of a motion can be connected to an image selector as described above, for example, and provide a criterion for selection or rejection to said image selector.

Preferably, however, beyond the mere determination of the existence of a motion, detection also includes a quantification of the motion. In one advantageous design, the motion detector is configured to detect the or components of the motion trajectory. Such a detection can already take place during the exposure and/or be reconstructed in a later step.

With regard to a subsequent reconstruction, the motion detector can be configured to allocate pixels of temporally sequential individual x-ray images to an identical section of the patient tissue in order thereby to detect motion occurring between the sequential exposure times. In other words, knowledge can be obtained of a motion trajectory by evaluating individual images produced over one or specific exposure times. The motion detector is therefore able, for example, to detect the trajectory of a relative motion between the x-ray emitter, the patient tissue and/or the x-ray sensor, in particular the relative trajectory between the image of the patient tissue in the sensor plane and the x-ray sensor.

A motion detector included in the x-ray imaging system can be embodied as a hardware component, preferably embodied as or comprising an acceleration sensor and/or an FPGA module or functionally identical or similar module. If the motion detector is embodied as a hardware component, in particular comprising an acceleration sensor, motion detection can already take place during exposure. It can also be provided that the motion detector comprises multiple acceleration sensors, wherein one acceleration sensor is, for example, associated with the x-ray emitter in order to detect the motion of said emitter, and one or more further acceleration sensors are associated with the x-ray sensor and/or the patient in order to detect the respective motion of said sensor or said patient. The motion detector can therefore also be able to detect absolute motion trajectories, for example, and, preferably, convert them to relative motion trajectories.

It can also be provided that the motion detector or components thereof are embodied as a computer program, wherein the program includes instructions that, when executed by a computer, cause said computer to detect a motion. In this case, or if the motion detector comprises an FPGA module or functionally identical or similar module, a reconstruction of a motion can be provided in a later step. A combination of such a design with one or more acceleration sensors is possible as well.

A detected motion, in particular a detected motion trajectory, can generally include the time profile of a position and/or include the time profile of an orientation. The motion detector can thus also be configured to, for example, detect the time profile of the tilting of the sensor plane with respect to the central beam.

The x-ray imaging system furthermore preferably comprises a motion compensator, wherein said motion compensator is configured to compensate a motion and thereby preferably harmonize the or some of the sequential individual x-ray images to one another. As discussed above, in the context of this application, the compensation of a motion is in particular the compensation of an effect of the motion on the individual x-ray images.

The motion to be compensated is in particular a motion detected by means of a motion detector. Specifically, the motion compensator can, for example, be configured to align the pixels (e.g. achieve congruence) of the temporally sequential individual x-ray images allocated by a motion detector to an identical section of the patient tissue by means of image transformation, in order to harmonize said x-ray images with one another.

It is possible, for example, for the respective motion of the emitter relative to the patient and the sensor to be determined via image recognition algorithms, in particular by means of the motion detector. By means of the motion compensator, one, several or every individual temporally sequential individual x-ray image can then be corrected according to the motion via image processing methods. An image processing method can include one or more geometric image transformations, e.g. translation, rotation, scaling, distortion or combinations thereof. It is possible, for example, for a plurality of first positions on a first individual x-ray image and a plurality of second positions on a second individual x-ray image to be identified as corresponding to one another with respect to the imaged patient tissue, and for at least one of the individual x-ray images to be transformed in such a way that the first and second positions are aligned (e.g. transformed such to be congruent).

In this way, in particular when a motion trajectory is known, motions or motion artifacts can be removed from one or more individual x-ray images by using an appropriate method.

A motion compensator included in the x-ray imaging system can be embodied as a hardware component, preferably comprising an FPGA module or functionally identical or similar module. In general, a hardware solution in which the focus and/or the detector move in opposite directions is possible. The motion compensator can, however, also be embodied as a computer program, which includes instructions that, when executed by a computer, cause said computer to compensate the motion.

The x-ray imaging system further preferably comprises an image combiner that is configured to combine the or some of the sequential, in particular harmonized, individual x-ray images to an overall x-ray image such that the respective exposures are merged.

The image combiner can in particular be configured to offset x-ray sensor signal values, which are associated with pixels of the temporally sequential, in particular harmonized, individual x-ray images, against one another in order to combine said x-ray images or parts thereof into an overall x-ray image. For example, the image combiner can be configured to perform a calculation based on x-ray sensor signal values, which are associated with pixels of the temporally sequential, in particular harmonized, individual x-ray images. Specifically, x-ray sensor signal values can be offset against one another by means of a weighted sum method. The overall x-ray image is then, in particular, an exposure-blended intraoral x-ray image with reduced motion blur or motion artifacts, which can be provided for diagnosis.

When the individual x-ray images are combined to the overall x-ray image, in particular by offsetting the signal values (e.g. performing calculations based on these values), the information about the patient tissue displayed by each individual x-ray images preferably is preserved and/or contributes to the overall x-ray image. In other words, the image contents of the individual x-ray images are combined. The individual x-ray images are therefore preferably used in their entirety. For example, all the pixels of the individual x-ray images or at least contiguous two-dimensional regions with a number of directly adjacent pixels (e.g. more than 10 percent or more than 50 percent or more than 90 percent of the total pixels) of the individual x-ray images can be included in the overall x-ray image. In particular analyzing only a plurality of individual pixels of a sensor or an individual x-ray image during or after an exposure may be unnecessary.

The image combiner can be embodied as a hardware component, preferably comprising an FPGA module or functionally identical or similar module, and/or embodied as a computer program, which includes instructions that, when executed by a computer, cause said computer to combine the respective individual x-ray images to the overall x-ray image.

A final x-ray image can accordingly be calculated from multiple individual images. The individual images originate in particular from one recording session. A recording session can, for example, be started by pressing a recording switch. Radiation can be subsequently generated in an automated manner and x-ray image information can be acquired. A final IO x-ray image can then be created for each recording session, in particular by means of the image optimizer, image selector, motion detector, motion compensator, image combiner or at least some of these components, which can also be integrated or consolidated into one or more common modules. An image processing system can, for example, comprise several or all of said components.

Since, as described, two, multiple or even many sequential individual x-ray images can be recorded using the x-ray imaging system, the x-ray imaging system is preferably configured to record the individual x-ray images quickly. The IO x-ray sensor is therefore preferably embodied as a rapid sensor.

The x-ray imaging system is in particular configured to respectively record the one or more sequential individual x-ray images in a time span that is less than 500 milliseconds, in particular less than 250 milliseconds, in particular less than 100 milliseconds, in particular less than 50 milliseconds, in particular less than 25 milliseconds, in particular less than 10 milliseconds, in particular less than 2.5 milliseconds, in particular less than 0.25 milliseconds, wherein multiple sequential individual x-ray images can in particular be recorded in time spans of different lengths. For example, the time span of an initially recorded x-ray image can be less than the time span of a subsequently recorded individual x-ray image.

The time span for the recording or acquisition of an individual x-ray image can in particular comprise an integration phase and a readout phase of the x-ray sensor. The x-ray imaging system is typically configured to record more individual x-ray images the shorter the time spans between the individual images.

The x-ray imaging system can therefore also be configured to record a series of temporally sequential individual x-ray images of the patient tissue, in particular record at least 2, in particular at least 3, in particular at least 10, in particular at least 100, in particular at least 1,000, in particular at least 10,000 temporally sequential individual x-ray images of the patient tissue.

The x-ray emitter, which emits x-ray radiation for recording the temporally sequential individual x-ray images, can operate in single operation, continuous operation, or pulsed operation. The x-ray imaging system can therefore be configured to record the temporally sequential individual x-ray images in a single operation, continuous operation, or pulsed operation of the x-ray emitter.

It can be provided that an individual x-ray image is recorded in a recording period between 10 and 100 milliseconds, for example, and that, for this purpose, the x-ray emitter emits radiation in single operation over a radiation period that is in particular of equal or lesser length than the recording period. After a time span, one further individual x-ray image, for example, can then be recorded in a recording period, e.g. between 0 and 500 milliseconds, whereby, for this purpose, the x-ray emitter again emits radiation in single operation over a radiation period that is in particular of equal or lesser length than the recording period.

It can, however, also be provided that, for example, at least 3, in particular at least 10, in particular at least 100, in particular at least 1,000, in particular at least 10,000 individual x-ray images are recorded in time spans between 0.1 and 10 milliseconds, and that the x-ray emitter operates in continuous operation or in a pulsed operation synchronous to said recording.

The exposure times for handheld x-ray emitters are generally longer due to the lower emitter output. In particular for handheld emitters, but also in general, the time period from the start of the first to the end of the last shot can be at least 0.25 seconds, in particular at least 0.5 seconds; it can, however, also be significantly more. This applies both in the case that a few longer recordings are carried out and in the case that several shorter recordings are carried out. X-ray recordings with radiation times that suggest that motion artifacts may occur should then be divided into individual recordings, which are then offset (e.g. calculated together). The x-ray imaging system can therefore generally be configured to record the temporally sequential individual x-ray images (in particular all of those) during a total time period of at least 0.25 seconds, in particular during a total time period of at least 0.5 seconds.

The x-ray imaging system can furthermore comprise an exposure analyzer, which is configured to analyze the exposure of at least one of the temporally sequential x-ray images.

The x-ray imaging system preferably also comprises a control device, which is configured to control the x-ray sensor and/or the x-ray emitter based on the analyzed exposure, preferably in such a way that the exposure, in particular the recording period (duration), of a further of the sequential individual x-ray images and/or the number of such further images is such that the overall x-ray image achieves a predetermined exposure range (intensity and/or level).

The x-ray imaging system can in particular be configured, based on the analyzed exposure, to determine whether the exposure has fallen short of a predetermined exposure range, and, if the exposure has fallen short of said exposure range, to control the x-ray sensor and/or the x-ray emitter in such a way that a) the acquisition of further temporally sequential individual x-ray images is continued and/or b) the predetermined exposure range is achieved with the subsequent individual x-ray image.

The x-ray imaging system can also be configured, based on the analyzed exposure, to determine whether the exposure has fallen short of a predetermined minimum exposure range, and, if the exposure has fallen short of said minimum exposure range, to control the x-ray sensor and/or the x-ray emitter in such a way that the acquisition of further temporally sequential individual x-ray images is ended. An early termination, in particular in the event of incorrect or inadequate positioning of the x-ray sensor and/or the x-ray emitter, can thus take place. This makes it possible to reduce the radiation exposure of the patient.

The x-ray imaging system can also be configured, based on the analyzed exposure of at least one, several or all of the thus far acquired individual x-ray images, to determine whether the exposure for this recording session has achieved or exceeded a predetermined exposure range, and, if the exposure has achieved or exceeded said exposure range, to control the x-ray sensor and/or the x-ray emitter in such a way that the acquisition of further temporally sequential individual x-ray images is ended in order to avoid unnecessary radiation exposure.

If an exposure analyzer is used, it can, for example, be provided that a first individual x-ray image (pre-exposure image) is recorded with a fixed time span, e.g. between 10 and 100 milliseconds, the exposure of said image is analyzed, and a second x-ray image (main exposure image) is subsequently recorded with a variable time span, e.g. between 0 and 500 milliseconds, wherein the variable time span depends on the exposure range of the first x-ray image.

The exposure analyzer can, however, also be configured to analyze the exposure continuously, e.g. during the recording of an individual x-ray image or during the recording of a series of individual x-ray images, for example when at least 3, in particular at least 10, in particular at least 100, in particular at least 1,000, in particular at least 10,000 x-ray images are recorded. The exposure analyzer can then analyze the exposure of multiple sequential individual x-ray images of the series, for example, and end the recording of further series images when a predefined exposure range is reached.

The exposure analyzer and the control device can therefore in particular form a unit for automatic exposure control (AEC). As described, for example at least two recordings (pre- and main exposure) can be created, which are added together in a later step to form one IO x-ray image. The two or more temporally sequential individual x-ray images can thus be used in a synergistic manner, both for the compensation of a motion (or motion artifacts) and for exposure control.

When an exposure analyzer is used to end further recordings, the x-ray imaging system can further be configured such that a forced break, in particular for repositioning the x-ray sensor and/or the x-ray emitter, occurs after the recording of further temporally sequential individual x-ray images is ended, wherein the forced break is in particular at least 0.5 seconds.

When an exposure analyzer is used to end further recordings, communication between the recording system and the emitter can serve to terminate the recording as soon as a critical number of individual images have been locally insufficiently exposed.

The x-ray imaging system, in particular the control device, can also be configured to synchronize a pulsed operation of the x-ray emitter with the x-ray image recording by the x-ray sensor. A connection between the sensor (recording system) and the emitter can be further provided for the purpose of synchronization, both for a continuous operation and for a pulsed operation. However, a connection between the sensor and the emitter may also be omitted (calibration recording can measure pulsed operation).

The exposure analyzer and/or the control device can again be embodied as a hardware component, preferably comprising an FPGA module or functionally identical or similar module and/or as a computer program, which includes instructions that, when executed by a computer, cause said computer to analyze the exposure.

The x-ray imaging system can further comprise the x-ray emitter that can be positioned outside the mouth of the patient in the beam path of which the intraoral x-ray sensor can be placed behind the patient tissue to be irradiated inside the mouth of the patient.

A holding system, which can be fastened or adapted to the x-ray emitter and/or the x-ray sensor in order to align the x-ray emitter in relation to the x-ray sensor, can be included as well. The holding system serves in particular as an adjustment aid for the x-ray emitter.

The invention further relates to a dental x-ray imaging method for producing an intraoral x-ray image with reduced motion blur, in particular by means of an x-ray imaging system as described above, wherein an intraoral x-ray sensor is placed behind patient tissue to be irradiated inside the mouth of a patient in the beam path of an, in particular hand-held, x-ray emitter positioned outside the mouth of the patient, and wherein two or more temporally sequential individual x-ray images of the patient tissue are recorded during respective exposures, and wherein an overall x-ray image is created from the or some of the temporally sequential individual x-ray images such that, on the one hand, the respective exposures are merged and, on the other hand, motion occurring between the sequential individual x-ray images is compensated so as to produce an exposure-blended intraoral x-ray image with reduced motion blur.

The invention further relates to a method for producing an x-ray image with reduced motion blur on an x-ray phantom, in particular by means of an x-ray imaging system as described above, wherein an x-ray phantom having a phantom structure to be irradiated is provided, which in particular simulates dental patient tissue, and wherein an intraoral x-ray sensor is placed behind the phantom structure to be irradiated in the beam path of an, in particular hand-held, x-ray emitter, and wherein two or more temporally sequential individual x-ray images of the phantom structure are recorded during respective exposures, and wherein an overall x-ray image is created from the or some of the temporally sequential individual x-ray images such that, on the one hand, the respective exposures are merged and, on the other hand, motion occurring between the exposures is compensated so as to produce an exposure-blended x-ray image with reduced motion blur.

The invention further relates to a method for the post-processing of temporally sequential intraoral individual x-ray images for producing an exposure-blended intraoral x-ray image with reduced motion blur, in particular by means of an x-ray imaging system as described above, wherein two or more temporally sequential intraoral individual x-ray images are read from a memory and wherein an overall x-ray image is created from the or some of the temporally sequential individual x-ray images such that, on the one hand, the respective exposures are merged and, on the other hand, motion occurring between the sequential x-ray images is compensated so as to produce an exposure-blended x-ray image with reduced motion blur.

The invention further also relates to a computer program for a dental x-ray imaging system as described above, or for a dental x-ray imaging method as described above, or for a method for producing an x-ray image on an x-ray phantom as described above, or for a method for the post-processing of intraoral individual x-ray images as described above, comprising: instructions that, when executed by a computer, cause said computer to record two or more temporally sequential individual x-ray images of patient tissue or a phantom structure during respective exposures and/or read said images from a memory, and/or instructions that, when executed by a computer, cause said computer to analyze the exposure of at least one of the sequential x-ray images, and/or instructions that, when executed by the computer, cause said computer to optimize the or at least one of the sequential x-ray images and/or the overall x-ray image by means of one or more dark current images, and/or instructions that, when executed by the computer, cause said computer to select or reject specific individual x-ray images from the or some of the sequential individual x-ray images, and/or instructions that, when executed by a computer, cause said computer to detect motion occurring between the or some of the sequential individual x-ray images, and/or instructions that, when executed by a computer, cause said computer to harmonize the or some of the sequential individual x-ray images with one another such that the motion is compensated, and/or instructions that, when executed by a computer, cause said computer to combine the or some of the sequential, in particular harmonized, individual x-ray images to one overall x-ray image.

Lastly, the invention relates to a data carrier or data signal comprising a computer program as described above.

BRIEF DESCRIPTION OF THE DRAWINGS

The figures show.

DETAILED DESCRIPTION OF THE INVENTION

Figure 1:
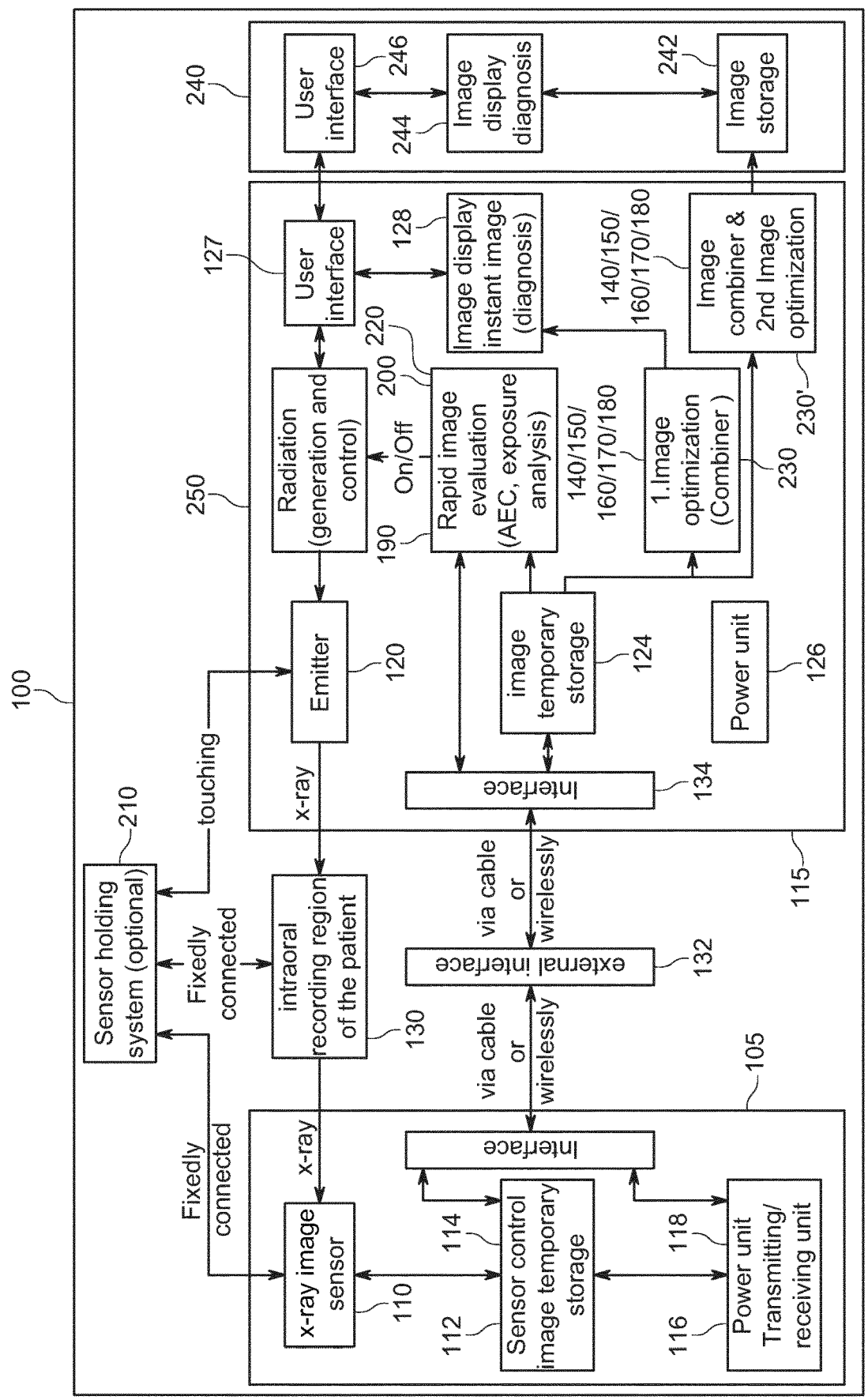
FIG. 1 a block diagram of an example of a dental x-ray imaging system,
FIG. 2 a time diagram of a first example of an operating mode of a dental x-ray imaging system,
FIG. 3 a time diagram of a second example of an operating mode of a dental x-ray imaging system.

With reference to FIG. 1, an x-ray imaging system 100 can comprise an intraorally placed x-ray sensor 110, which is configured to detect x-rays of an extraorally placed x-ray emitter 120. Before impinging on the x-ray sensor 110, the x-rays pass through an intraoral recording region of the patient 130, so that the x-ray sensor is capable of recording an x-ray image of the patient tissue. A sensor holding system 210 can be fixedly attachable to the x-ray sensor 110. The sensor holding system 210 can furthermore be securable to the patient, in particular to the mouth of the patient, so that the x-ray sensor 110 is substantially fixed via the holding system 210 in relation to the patient tissue 130 to be irradiated. The holding system 210 can further comprise a positioning aid for the x-ray emitter 120, which preferably projects from the mouth of the patient and forms a, for example, ring-shaped structure, e.g. with a respective contact surface, to which the x-ray emitter 120 can be guided, in particular with its tube, in order to ensure a correct alignment of the emerging x-rays.

In the depicted example, the x-ray sensor 110 is part of an x-ray sensor unit 105 (which is sometimes also referred to as x-ray sensor for short) having a housing, which can be placed inside the mouth of the patient and can contain further components. An x-ray sensor unit 105 can comprise a sensor control 112, for example, which can be configured to control the sensor, in particular depending on predefined criteria, in such a way that x-rays are acquired (integration phase) and/or that an x-ray image is output in the form of x-ray sensor signal values (readout phase). Individual x-ray images acquired by the x-ray sensor can then be temporarily stored in an image memory 114. An x-ray sensor unit 105 can further comprise a power unit 116, which supplies other components, in particular the sensor control 112, the image memory 114 and/or the x-ray sensor 110, with electrical energy. A transmitting/receiving unit 118, which allows an in particular wireless transmission of x-ray images, can be provided as well. The above-described components can, however, also be provided outside the x-ray sensor unit 105 and may optionally form independent units or be included in another unit. An option, for example, is an external interface 132, for example, which is used between the sensor and the emitter unit, i.e. is physically decoupled from these two components. When appropriate, the sensor can then be made smaller. This may provide advantages in terms of space and cost. In order to ensure the above-described transmission, such an external interface can be connected to an internal interface 134 by means of a cable or wirelessly.

In the depicted example, the x-ray emitter 120 is part of an x-ray emitter unit 115 (which is sometimes also referred to as x-ray emitter for short) which can again comprise a separate housing, in which further components can be located. An x-ray emitter unit 115 can comprise an emitter control 122, for example, which can be configured to activate or deactivate the emitter. The emitter control 122 can be connected to the sensor control 112. The x-ray emitter unit 115 can further comprise an image memory 124. The x-ray imaging system 100 can be configured to transmit individual x-ray images from the image memory 114 of the sensor unit 105 to the image memory 124 of the emitter unit 115. For this purpose, a connection of the two units can be provided via a cable, for example, or transmission can take place by means of the transmitting/receiving unit 118. The emitter unit 115 preferably further comprises a power unit 126, which supplies other components, in particular those described above or below, with electrical energy. To control the x-ray emitter 120 and/or to set radiation parameters, the emitter unit 115 can also comprise a user interface 127. In one preferred embodiment, the emitter unit 115 is embodied as a handheld x-ray emitter 250.

The x-ray imaging system 100, in particular the x-ray emitter unit 115, can furthermore comprise an image evaluation unit 220 that may be configured for rapid image evaluation and may have an exposure analyzer 190. The exposure range of an individual x-ray image, which is temporarily stored in the image memory 124, for example, can be analyzed by means of the exposure analyzer 190. Depending on the exposure range, a control signal to control the x-ray emitter such that the exposure range of further individual x-ray images and/or the number of further x-ray images is affected can be sent to the emitter control 122. The control signal can also be an on/off signal to activate or deactivate the emitter.

The x-ray imaging system 100, in particular the x-ray emitter unit 115, can also include one or more image processing units 230, 230'. An image processing unit can in particular include an image optimizer 140, an image selector 150, a motion detector 160, a motion compensator 170, and/or an image combiner 180. To optimize individual x-ray images present in the image memory 124 as raw data, for example by means of dark current images, the image processing unit 230 can, for example, comprise an image optimizer 140. To compensate a motion, in particular by means of image transformations, said image processing unit 230 can further comprise a motion detector 160 and/or motion compensator 170. To combine multiple individual x-ray images after compensation of the motion by merging the exposures to one final exposure-blended IO x-ray image with reduced motion blur, said image processing unit 230 can further comprise an image combiner 180. An image processing unit thus receives analog or digital x-ray image information and processes said information, e.g. via image optimization. The information can furthermore be archived and/or displayed.

A final IO x-ray image can, for example, be displayed directly by means of an image display unit 128, which can be part of the emitter unit 115 (instant image). The image processing unit 230 for producing the final IO x-ray image for direct display can, for example, work with limited resolution. An image processing unit 230' for producing the final IO x-ray image for external display, for example on a computer 240 having an image memory 242, an image display unit 244, and, if appropriate, a user interface 246, can be provided as well.

The components described above as a part of the x-ray emitter unit 115 can also be provided outside the x-ray emitter unit 115 and may optionally form independent units or be included in another unit. An image processing unit 230' can, for example, also be embodied as part of the computer 240.

In the context of this application, the x-ray sensor that can be placed in the mouth is generally to be understood as an x-ray sensor 110 in the narrower sense. In the broader sense, however, the x-ray sensor can also be placeable in the mouth with the housing and, if applicable, further components (x-ray sensor unit 105). Correspondingly, the x-ray emitter is generally to be understood as the emitter 120 in the narrower sense, i.e. for example an x-ray tube or a component comprising an x-ray tube. In a broader sense however, the x-ray emitter can also be positioned outside the mouth with the housing and, if applicable, further components (x-ray emitter unit 115, handheld x-ray emitter 250).

Figure 2:
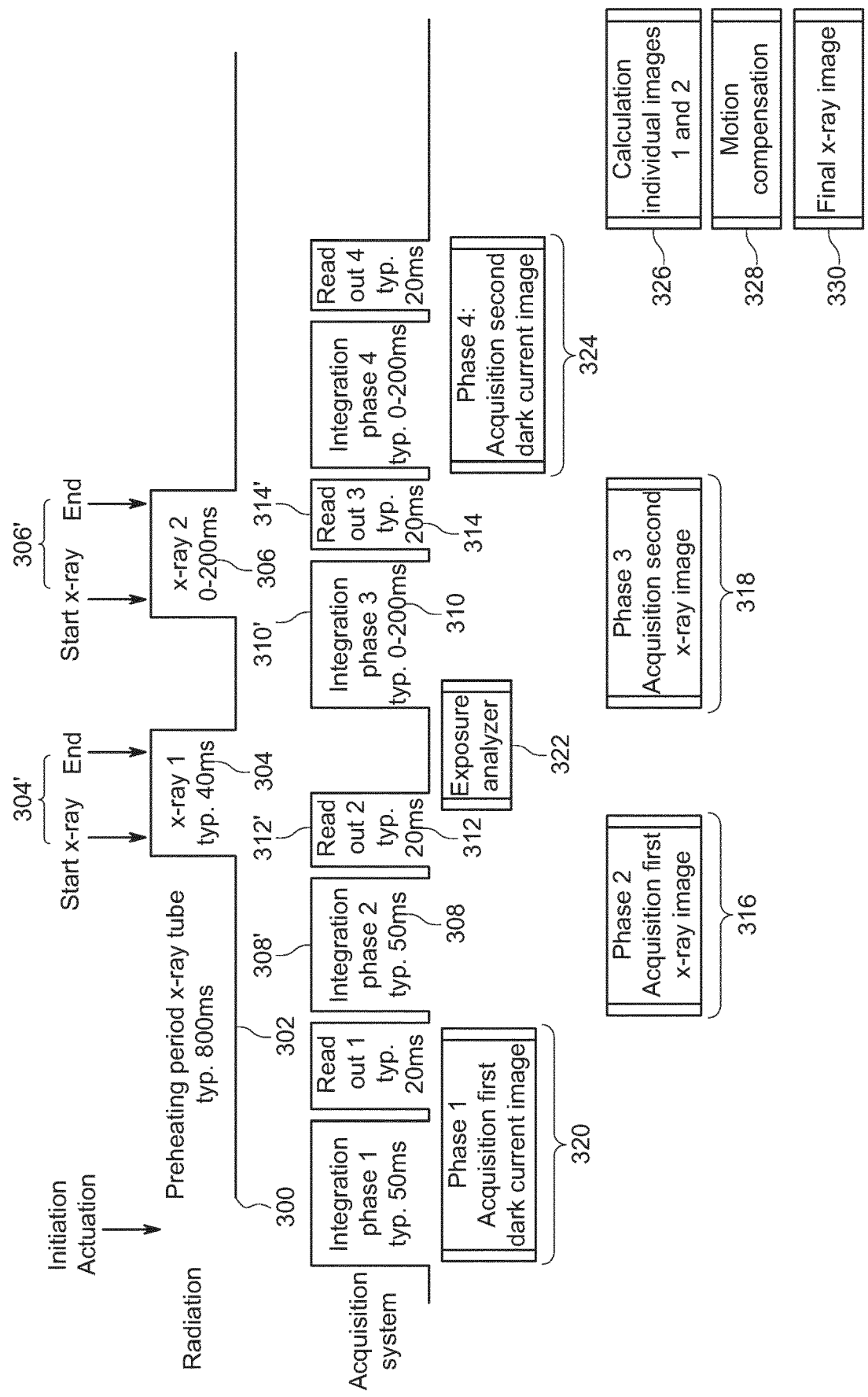

With reference to FIG. 2, an x-ray imaging system can be configured as an example of the operating mode presented in the following. An (x-ray) recording session can initially be started by actuating a recording switch. An initiation of actuation 300 can thus take place. A preheating period 302 can be provided, in which the x-ray emitter or x-ray tube is warmed prior to the application of a high voltage, preferably for a time period between 400 and 1,600 milliseconds, e.g. 800 milliseconds. The preheating period serves in particular to ensure reproducible radiation after a high voltage is added. At least two sequential exposures 304, 306 can then take place, for example, in which the x-ray radiation is active for a respective radiation period 304', 306'. The first radiation period 304' can be between 0 and 80 milliseconds, e.g. 40 milliseconds. The second radiation period can be between 0 and 500, e.g. between 0 and 200, milliseconds. The exposure time can in particular represent the exposure duration over which the x-ray radiation extends. Exposure is a process in which a detector medium is exposed to the x-ray radiation. For IO x-raying, the exposure time can also be between 10 and 500 milliseconds for example, in particular between 50 and 200 milliseconds.

During the emission of x-ray radiation, the x-ray sensor can be in a respective integration mode 308, 310 for multiple sequential integration periods 308', 310' in order to acquire said x-ray radiation. The respective integration periods 308', 310' are preferably at least as long as the associated radiation periods 304', 306'. Each integration phase 308, 310 is preferably followed by a readout phase 312, 314, which respectively extends over the readout period 312', 314'. One integration period and a subsequent readout period respectively contribute to the recording period (image acquisition) 316, 318 for one x-ray image. In other words, the recording period, i.e. the image acquisition, in particular includes the exposure process and the subsequent readout from the sensor. It can, for example, be provided that a first x-ray image is recorded during a recording period that comprises an integration period between 10 and 100 milliseconds, e.g. 50 milliseconds, and a readout period between 5 and 50 milliseconds, e.g. 20 milliseconds.

The individual x-ray image can then be subjected to an exposure analysis 322 by means of an exposure analyzer. The intensity of one or more received x-ray images is thereby evaluated in order to achieve a specified exposure quality or predetermined exposure range (intensity). Depending on such evaluation, a second individual x-ray image can then be recorded. It can, for example, be provided that a second x-ray image is recorded during a recording period that comprises an integration period between 0 and 500 milliseconds, e.g. 200 milliseconds, and a readout period between 5 and 50 milliseconds, e.g. 20 milliseconds.

One or more dark current images can be recorded during corresponding recording periods 320, 324 before and/or after the recording of the temporally sequential x-ray images, wherein a respective integration phase and a readout phase are provided in each case here as well.

After at least two temporally sequential x-ray images have been recorded, an optimization 326 of the individual images can be carried out, in particular by offsetting said images with the dark current image or images, e.g. by performing a calculation based on the respective individual images and the dark current image. A motion compensation 328 can then be carried out in order to obtain ultimately a final IO x-ray image 330 by means of combination.

A final IO x-ray image is thus the product of an x-ray imaging system and represents an intraorally created x-ray depiction. Just as for the individual temporally sequential x-ray images, the smallest spatial resolution is broken up with image pixels. The generation proceeds through different phases as described, in particular after digitization as an unprocessed data collection (e.g. 16 bits, perhaps based on multiple exposures) to storage as a processed, filtered, (un)compressed data set with histogram compensation (e.g. 8 bits). From the user's point of view, an x-ray image is ultimately displayed or printed as a black/white negative 2D rendering, e.g. on a monitor or on a film. Reduced motion blur or a reduction of motion artifacts is achieved in a final x-ray image as described, whereby it is also possible that artifacts appear due to the processing of the image. A final x-ray image is thus an exposure-blended image with reduced motion blur or reduced motion artifacts.

In summary, therefore, after the initiation of a recording session, in particular by actuating a switch, radiation is subsequently generated in an automated manner and x-ray image information is acquired. One final IO x-ray image can in particular be created per recording session.

Figure 3:
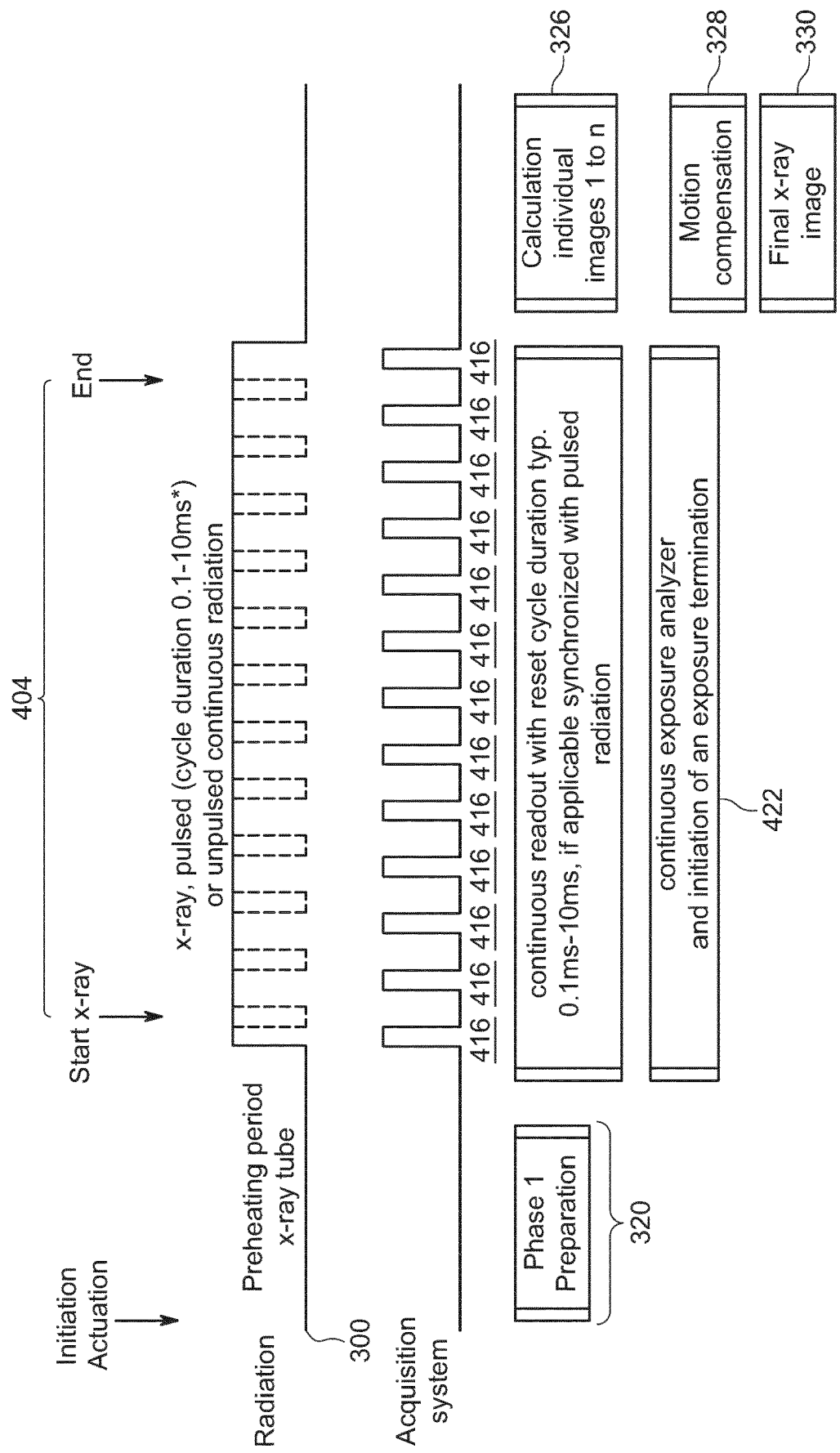

With reference to FIG. 3, an x-ray imaging system can also be configured as an example of the operating mode presented in the following. To begin with, an initiation of actuation 300 can again take place and a preheating period 302 of the x-ray tube can be provided. Unpulsed continuous radiation or pulsed radiation 404 over a radiation period 404', e.g. with a cycle duration between 0.1 and 10 milliseconds, can subsequently be provided.

During the radiation period 404', the x-ray sensor can record several or a large number of sequential x-ray images during respective recording periods 416, whereby the recording periods 416 in particular again comprise respective integration and readout periods. In this operating mode, the recording periods 416 can in particular be between 0.1 and 10 milliseconds. During a pulsed operation of the emitter, said recording periods are preferably synchronized with the emitter.

The individual x-ray images can be subjected to a continuous exposure analysis 422 by means of an exposure analyzer. The intensity of the x-ray images can thereby be evaluated, in particular in sum, in order to abort the recording of further individual x-ray images as soon as a predefined intensity is reached. Depending on the exposure range, the number of further x-ray images can additionally be determined.

After a number of temporally sequential individual x-ray images have been recorded, an optimization 326 of the individual images, a motion compensation 328, and ultimately the production of a final IO x-ray image 330 by means of combination can again be carried out.

To the person skilled in the art it is obvious that the above-described embodiments are only examples and the invention is not limited to them, but can instead be varied in a multitude of ways without departing from the scope of protection of the claims. It is furthermore obvious that, independent of whether they are disclosed in the description, the claims, the figures, or otherwise, the features also individually define essential components of the invention, even if they are jointly described alongside other features, and can thus be regarded as being disclosed independently of one another. The description of features of one design example also respectively applies to the other design examples.

LIST OF REFERENCE NUMBERS 100 x-ray imaging system
105 x-ray sensor unit
110 intraoral x-ray sensor
112 sensor control
114 image memory of the sensor unit
115 x-ray emitter unit
116 power unit for the sensor unit
118 transmitting/receiving unit
120 x-ray emitter
122 emitter control
124 image memory of the emitter unit
126 power unit for the emitter unit
127 user interface
128 image display unit
130 patient tissue to be irradiated
132 external interface
134 internal interface
140 image optimizer
150 image selector
160 motion detector
170 motion compensator
180 image combiner
190 exposure analyzer
200 control device
210 holding system
220 image evaluation unit
230, 230' image processing unit
240 computer
242 image memory of the computer
244 image display unit of the computer
246 user interface of the computer
250 handheld x-ray emitter
300 initiation of actuation
302 preheating period
304, 306, 404 exposure
304', 306', 404' radiation period
308, 310 integration mode
308', 310' integration period
312, 314 readout mode
312', 314' readout period
316, 318, 324, 416 recording period
322, 422 exposure analysis
326 optimization
328 motion compensation
330 final IO x-ray images

The invention claimed is:

1. A dental x-ray imaging system for producing an intraoral x-ray image with reduced motion blur comprising:
   an intraoral x-ray sensor, which can be placed inside the mouth of a patient, in the beam path of a handheld x-ray emitter positioned outside the mouth of the patient, and behind patient tissue to be irradiated,
   wherein the x-ray imaging system is configured to record two or more temporally sequential individual x-ray images of the patient tissue during respective exposures in a recording session, and
   wherein the x-ray imaging system is configured to create an overall x-ray image from the or some of the temporally sequential individual x-ray images such that the results of the respective exposures are merged and a motion occurring between and/or during the sequential individual x-ray images is compensated so as to produce an exposure-blended intraoral x-ray image with reduced motion blur.

2. The dental x-ray imaging system according to claim 1, wherein an image optimizer is included, which is configured to optimize the or at least one of the sequential individual x-ray images and/or the overall x-ray image of the patient tissue by means of one or more dark current images, and/or
   wherein an image selector is included, which is configured to select or reject specific individual x-ray images from the or some of the sequential individual x-ray images, and/or
   wherein a motion detector is included, which is configured to detect a motion occurring between and/or during the or some of the sequential individual x-ray images, and/or
   wherein a motion compensator is included, which is configured to harmonize the or some of the sequential individual x-ray images with one another such that the motion is compensated, and/or
   wherein an image combiner is included, which is configured to combine the or some of the sequential, in particular harmonized, x-ray images to the overall x-ray image such that the results of the respective individual exposures are merged.

3. The dental x-ray imaging system according to claim 1, wherein the x-ray imaging system is configured to record the or at least one of the sequential individual x-ray images during a time span that is less than 250 milliseconds, in particular less than 25 milliseconds, in particular less than 2.5 milliseconds, in particular less than 0.25 milliseconds.

4. The dental x-ray imaging system according to claim 1, wherein the x-ray imaging system is configured to record a series of temporally sequential individual x-ray images of the patient tissue, in particular at least 2 temporally sequential individual x-ray images of the patient tissue, and/or
   wherein the x-ray imaging system is configured to record the temporally sequential individual x-ray images during a pulsed operation of the x-ray emitter.

5. The dental x-ray imaging system according to claim 1, wherein an exposure analyzer is included, which is configured to analyze the result of the exposure of at least one, several or all of the thus far acquired temporally sequential individual x-ray images, and
   wherein a control device is included, which is configured to control the x-ray sensor and/or the x-ray emitter based on the analyzed result of the exposure, in particular in such a way that the exposure of a further of the sequential individual x-ray images and/or the number of said further images is such that the overall x-ray image achieves a predetermined exposure range.

6. The dental x-ray imaging system according to claim 5, wherein, the x-ray imaging system is configured to determine, based on the analyzed result of the exposure of at least one, several or all of the thus far acquired individual x-ray images, whether the exposure for this recording session has fallen short of a predetermined exposure range, and, if the exposure has fallen short of said exposure range, to control the x-ray sensor and/or the x-ray emitter in such a way that a) the acquisition of further temporally sequential individual x-ray images is continued and/or b) the subsequent individual x-ray image achieves the predetermined exposure range, and/or wherein the x-ray imaging system is configured, based on the analyzed exposure of at least one, several or all of the thus far acquired individual x-ray images, to determine whether the exposure for this recording session has fallen short of a predetermined minimum exposure range, and, if the exposure has fallen short of said minimum exposure range, to control the x-ray sensor and/or the x-ray emitter in such a way that the acquisition of further temporally sequential individual x-ray images is ended in order to avoid unnecessary radiation exposure and/or wherein the x-ray imaging system is configured, based on the analyzed exposure of at least one, several or all of the thus far acquired individual x-ray images, to determine whether the exposure for this recording session has achieved or exceeded a predetermined exposure range, and, if the exposure has achieved or exceeded said exposure range, to control the x-ray sensor and/or the x-ray emitter in such a way that the acquisition of further temporally sequential individual x-ray images is ended in order to avoid unnecessary radiation exposure.

7. The dental x-ray imaging system according to claim 2, wherein the image optimizer is configured to perform a calculation based on both x-ray sensor signal values associated with pixels of a dark current image and x-ray sensor signal values associated with pixels of one of the sequential x-ray images and/or the overall x-ray image of the patient tissue in order to optimize the x-ray image, and/or wherein the image selector is configured to evaluate the or some of the sequential individual x-ray images using predefined criteria in order to select from among them suitable, in particular sufficiently congruent, individual x-ray images or reject unsuitable, in particular overly incongruent individual x-ray images, and/or wherein the motion detector is configured to allocate pixels of temporally sequential individual x-ray images to a substantially identical section of the patient tissue in order to detect the motion occurring between and/or during the sequential individual x-ray images, and/or wherein the motion compensator is configured to align, particularly bring to congruence, the pixels of the temporally sequential individual x-ray images allocated to the substantially identical section of the patient tissue by means of image transformation, in order to harmonize these x-ray images with one another and/or wherein the image combiner is configured to perform a calculation based on x-ray sensor signal values of corresponding pixels of the temporally sequential, in particular harmonized, individual x-ray images in order to combine these individual x-ray images to the overall x-ray image.

8. The dental x-ray imaging system according to claim 2, wherein an exposure analyzer is included, which is configured to analyze the result of the exposure of at least one, several or all of the thus far acquired temporally sequential individual x-ray images, wherein the exposure analyzer is embodied as a computer program, which includes instructions that, when executed by a computer, cause said computer to analyze the result of the exposure, and/or wherein the image optimizer is embodied as a computer program, which includes instructions that, when executed by a computer, cause said computer to optimize the individual x-ray images and/or the overall x-ray image of the patient tissue by means of dark current compensation, and/or wherein the image selector is embodied as a computer program, which includes instructions that, when executed by a computer, cause said computer to select or reject individual x-ray images, and/or wherein the motion detector is embodied as a computer program, which includes instructions that, when executed by a computer, cause said computer to detect the motion, and/or wherein the motion compensator is embodied as a computer program, which includes instructions that, when executed by a computer, cause said computer to compensate the motion, and/or wherein the image combiner is embodied as a computer program, which includes instructions that, when executed by a computer, cause said computer to combine the respective individual x-ray images to the overall x-ray image.

9. The dental x-ray imaging system according to claim 2, wherein an exposure analyzer is included, which is configured to analyze the result of the exposure of at least one, several or all of the thus far acquired temporally sequential individual x-ray images, wherein the exposure analyzer is embodied as a hardware component, preferably comprising an FPGA module or functionally similar module, and/or wherein the image optimizer is embodied as a hardware component, preferably comprising an FPGA module or functionally similar module, and/or wherein the image selector is embodied as a hardware component, preferably comprising an FPGA module or functionally similar module and/or an acceleration sensor, and/or wherein the motion detector is embodied as a hardware component, preferably comprising an FPGA module or functionally similar module and/or an acceleration sensor, and/or wherein the motion compensator is embodied as a hardware component, preferably comprising an FPGA module or functionally similar module, and/or wherein the image combiner is embodied as a hardware component, preferably comprising an FPGA module or functionally similar module.

10. The dental x-ray imaging system according to claim 1, wherein a holding system is included, which can be fastened or adapted to the x-ray emitter and/or x-ray sensor in order to align the x-ray emitter in relation to the x-ray sensor.

11. A dental x-ray imaging method for producing an intraoral x-ray image with reduced motion blur, in particular by means of an x-ray imaging system according to claim 1,
wherein an intraoral x-ray sensor is placed inside the mouth of a patient, in the beam path of an, in particular handheld, x-ray emitter positioned outside the mouth of the patient, and behind patient tissue to be irradiated, and
wherein two or more temporally sequential individual x-ray images of the patient tissue are recorded during respective exposures, and
wherein an overall x-ray image is created from the or some of the temporally sequential individual x-ray images such that the results of the respective exposures are merged and a motion occurring between and/or during the sequential individual x-ray images is compensated so as to produce an exposure-blended intraoral x-ray image with reduced motion blur.

12. A method for producing an x-ray image with reduced motion blur on an x-ray phantom, in particular by means of an x-ray imaging system according to claim 1,
wherein an x-ray phantom having a phantom structure to be irradiated is provided, which in particular simulates dental patient tissue, and
wherein an intraoral x-ray sensor is placed behind the phantom structure to be irradiated in the beam path of an, in particular handheld, x-ray emitter, and
wherein two or more temporally sequential individual x-ray images of the phantom structure are recorded during respective exposures, and
wherein an overall x-ray image is created from the or some of the temporally sequential individual x-ray images such that the results of the respective exposures are merged and a motion occurring between and/or during the exposures is compensated so as to produce an exposure-blended x-ray image with reduced motion blur.

13. A method for the post-processing of temporally sequential intraoral individual x-ray images for producing an exposure-blended intraoral x-ray image with reduced motion blur, in particular by means of an x-ray imaging system according to claim 1,
wherein two or more temporally sequential intraoral individual x-ray images are read from a memory and
wherein an overall x-ray image is created from the or some of the temporally sequential individual x-ray images such that the results of the respective exposures are merged and a motion occurring between and/or during the sequential individual x-ray images is compensated so as to produce an exposure-blended x-ray image with reduced motion blur.

14. A non-transitory computer readable medium comprising a computer program, that when executed on a computer of a dental X-ray imaging system causes the computer to execute:
instructions that, when executed by said computer, cause said computer to record two or more temporally sequential individual x-ray images of patient tissue or a phantom structure during respective exposures and/or read said images from a memory, and/or
instructions that, when executed by a computer, cause said computer to analyze the result of the exposure of at least one of the sequential individual x-ray images, and/or
instructions that, when executed by the computer, cause said computer to optimize the or at least one of the sequential individual x-ray images and/or the overall x-ray image by means of one or more dark current images and/or
instructions that, when executed by the computer, cause said computer to select or reject specific individual x-ray images from the or some of the sequential individual x-ray images, and/or
instructions that, when executed by a computer, cause said computer to detect a motion occurring between and/or during the or some of the sequential individual x-ray images, and/or
instructions that, when executed by a computer, cause said computer to harmonize the or some of the sequential individual x-ray images with one another such that the motion is compensated, and/or
instructions that, when executed by a computer, cause said computer to combine the or some of the sequential, in particular harmonized, individual x-ray images to an overall x-ray image.

15. A non-transitory computer readable medium comprising a computer program, that when executed on a dental X-ray imaging system carries out a method according to claim 14.

* * * * *